United States Patent [19]

Raccach

[11] 4,303,679
[45] Dec. 1, 1981

[54] METHOD AND BACTERIAL COMPOSITIONS FOR FERMENTING MEATS

[75] Inventor: Moshe Raccach, Sarasota, Fla.

[73] Assignee: Microlife Technics, Inc., Sarasota, Fla.

[21] Appl. No.: 114,760

[22] Filed: Jan. 24, 1980

[51] Int. Cl.$^3$ .................. A23B 4/12; A23C 11/00; C12P 7/56; C12N 1/20

[52] U.S. Cl. .................................. 426/59; 426/56; 435/139; 435/253; 435/822

[58] Field of Search .............. 435/139, 822, 253; 426/56, 59

[56] References Cited

U.S. PATENT DOCUMENTS

| | | | |
|---|---|---|---|
| 2,907,661 | 10/1959 | Niven, Jr. et al. | 426/56 |
| 2,945,766 | 7/1960 | Chaiet | 426/59 |
| 3,561,977 | 2/1971 | Rothchild et al. | 426/59 |
| 3,960,664 | 6/1976 | Olsen et al. | 426/59 |
| 4,147,807 | 4/1979 | Gryczka et al. | 426/56 |
| 4,160,038 | 7/1979 | Groben et al. | 426/56 X |
| 4,238,513 | 12/1980 | Satz | 426/59 |

OTHER PUBLICATIONS

Bergey's (6th Ed., 1948), pp. 249 and 250.
ATCC Catalog (1976) p. 93.
Pederson, Bacteriological Review, vol. 13, pp. 225–232, (1949).
Garvie, International Journal of Systemic Bacteriology, vol. 24, No. 2, pp. 301–306, (Apr. 1974).
Pederson et al, N.Y. State Agr. Exp. Station Technical Bulletin, No. 288, Jul. 1949, (29 pages).
Kirk–Othmer, vol. 2, pp. 593–596 (1963).

*Primary Examiner*—Lionel M. Shapiro
*Attorney, Agent, or Firm*—Ian C. McLeod

[57] ABSTRACT

A method and bacterial compositions are described for producing fermented meat by generating lactic acid using selected cultures of *Pediococcus pentosaceus* which have unique low temperature meat fermentation characteristics. The preferred *Pediococcus pentosaceus* is NRRL-B-11,465 which is unusually rapid in lowering the pH at low meat temperatures. A stimulatory, edible metal salt, preferably a manganese salt, is provided in the meat with the *Pediococcus pentosaceus* to reduce or eliminate preservative inhibition and/or to accelerate growth at meat temperatures between 15.6° C. (60° F.) to 26.7° C. (80° F.). Preservatives to prevent spoilage and rancidity can be used in the meat and can include hydroxyaryl antioxidants, particularly butylated hydroxytoluene (BHT) and/or butylated hydroxyanisole (BHA). BHT and/or BHA together with other meat preservatives, particularly sodium chloride, severely inhibit NRRL-B-11,465 at low meat temperatures between 15.6° C. (60° F.) and 26.7° C. (80° F.). *Pediococcus pentosaceus* compositions containing the stimulatory metal salt are also described. The method and compositions, particularly with a manganese salt, can produce a pH of less than about 5.0 in less than 30 hours at smokehouse temperatures above about 15.6° C. (60° F.) and at initial meat temperatures of 4.4° C. to 10° C. (40° to 50° F.) with standard casing diameters (up to about 100 mm). *Pediococcus pentosaceus* NRRL-B-11,465 is particularly adapted for low temperature meat fermentation and rapidly lowers the pH in the meat to about 4.3 under these conditions with sufficient added assimilable carbohydrate. The method is particularly useful for making dry and semi-dry sausage as well as for nitrite reduction in meats due to the lowering of the pH.

19 Claims, No Drawings

METHOD AND BACTERIAL COMPOSITIONS FOR FERMENTING MEATS

BACKGROUND OF THE INVENTION

The present invention relates to a method and to bacterial compositions for fermenting meat using selected cultures of *Pediococcus pentosaceus* having rapid fermentation characteristics at meat temperatures of between 15.6° C. (60° F.) and 26.7° C. (80° F.) especially in the presence of a stimulatory metal ion preferably a manganese ion. Smokehouse temperatures in the range between about 15.6° C. (60° F.) and 48.9° C. (120° F.) can be used; however, lower temperatures than 26.7° C. (80° F.) are preferred to reduce the risk of significant *Staphylococcus aureus* growth in the meat. In particular, the present invention relates to novel selected *Pediococcus pentosaceus* compositions containing a stimulatory metal salt which have the ability to rapidly ferment in meat in the presence of an assimilable carbohydrate and preservatives such as a hydroxyaryl antioxidant, particularly butylated hydroxytoluene (BHT) or butylated hydroxyanisole (BHA) or mixtures thereof, at meat temperatures between 15.6° C. (60° F.) to 26.7° C. (80° F.) to produce a pH of less than about 5.0.

PRIOR ART

The prior art has generally described meat fermentation methods using many different strains of the genus Pediococcus which generate lactic acid in the meat. U.S. Pat. No. 2,907,661 to Niven et al (1959) and U.S. Pat. Nos. 3,561,977 and 3,910,664 to Rothchild et al are representative of this prior art which is extensive. Also it is common practice particularly in the United States and some countries abroad, to use BHT, BHA or mixtures thereof, or other hydroxyaryl type antioxidants along with nitrites, nitrates and/or sodium chloride, or other preservative compounds to prevent spoilage and rancidity of fermented meat products, particularly dry sausage, which may be refrigerated or frozen for long periods. The antioxidants prevent rancidity in the stored fats. These preservatives have been found to be quite toxic to Pediococcus depending upon the species and/or upon the type and concentration of the preservatives and the fermentation temperatures.

Usually, semi-dry sausage is prepared by being fermented with a carbohydrate, particularly dextrose and/or naturally occurring glycogen, in the meat in less than about 30 hours and dry sausage is fermented over a period of two to three days. Both methods preferably involve a rapid initial fermentation to produce the lactice acid in the meat thereby lowering the pH. In general, the prior art strains of Pediococcus used for making sausages to develop a pH of less than about 5.0 in about 30 hours or less must be fermented at an elevated meat temperature range between about 26.7° to 48.9° C. (80° F. to 120° F.). These strains of Pediococcus are too slow at meat temperatures between about 15.6° C. to 26.7° C. (60° F. to 80° F.) and take much longer to develop a pH of less than about 5.0 in this temperature range. Thus at least 48 hours at 26.7° C. (80° F.) is required to achieve a pH of 5.0 or lower with *Pediococcus acidilactici* or *Pediococcus cerevisiae* (latter now known as *Pediococcus damnosus*). There has been no known species of Pediococcus which is commercially useful for rapid fermentations in the temperature range between 15.6° C. to 26.7° C. (60° F. to 80° F.) in the meat to lower the pH to less than 5.0 in less than 30 hours, particularly in the presence of rancidity inhibiting hydroxyaryl antioxidant preservatives. It is believed that there has been no suggestion by the prior art that any strain of *Pediococcus pentosaceus* is useful for making sausage.

U.S. Pat. No. 2,945,766 to Chaiet describes the use of manganese salts in the fermentation of meat using various species of Pediococcus, particularly *Pediococcus acidilactici* or *Pediococcus cerevisiae*, at manganese levels of 0.5 to 4 percent by weight of the culture. The bacteria are grown in the presence of a manganese salt, and/or it is added to the culture or to the meat formulation. The result of using this prior art method is that the amount of starter culture needed per unit weight of meat is decreased and the acidity produced in the meat per unit weight of starter culture is increased. The meat fermentation is conducted at smokehouse temperatures between 26.7° C. (80° F.) to 43.3° C. (110° F.). Chaiet does not disclose the use of BHT or BHA or other antioxidants or meat temperatures for fermentation below 26.7° C. (80° F.).

The prior art is also faced with a problem in the reduction of residual nitrite in meats after curing which generates the identifiable red color in the meat. The nitrites can form nitrosamines in meats upon frying which are thought to be a health hazard. Acids are known to destroy nitrites. The problem is to be able to rapidly generate sufficient acidity in the meat to aid in the reduction of nitrites particularly at meat temperatures of about 26.7° C. (80° F.) or less.

OBJECTS

It is therefore an object of the present invention to provide a method of producing fermented meats, including semi-dry and dry sausage and hams, using a selected culture of *Pediococcus pentosaceus*, particularly in the presence of a stimulatory food grade metal salt, which is useful at low meat temperatures between about 15.6° C. to 26.7° C. (60° F. to 80° F.) to rapidly lower the pH to less than about 5, particularly in the presence of hydroxyaryl type antioxidants such as BHT, BHA or mixtures thereof along with other preservatives. It is further an object to provide novel bacterial concentrates of the selected *Pediococcus pentosaceus* cultures containing a stimulatory food grade metal salt to be used in the method. Further still, it is an object to provide a method and concentrates which are useful to induce rapid nitrite reduction in meats at low meat temperatures because of the generation of lactic acid. These and other objects will become increasingly apparent by reference to the following description.

GENERAL DESCRIPTION

The present invention uses *Pediococcus pentosaceus* for making sausage. In particular, the present invention relates to the improvement in a meat fermentation method including the steps of providing lactic acid producing bacteria in the meat with an assimilable carbohydrate, usually with meat spoilage and rancidity inhibiting preservatives, and then fermenting the meat with the bacteria so that lactic acid is produced from the carbohydrate over a period of time in the fermented meat which comprises providing in admixture in meat a culture of a selected *Pediococcus pentosaceus*, usually at a concentration of between about $10^5$ and $10^9$ of the *Pediococcus pentosaceus* per gram of meat, with an assimilable carbohydrate, especially with spoilage inhibiting amounts of preservatives, and with a stimulatory food grade metal salt, preferably a manganese salt, in an amount sufficient to accelerate the fermentation by the *Pediococcus pentosaceus*, wherein the selected *Pediococcus pentosaceus* culture is characterized by an ability to rapidly ferment in the meat admixture at meat temperatures between about 15.6° C. (60° F.) and 26.7° C. (80° F.) to produce a pH less than about 5; and fermenting the meat admixture at temperatures between about 15.6° C. (60° F.) and 48.9° C. (120° F.) with the *Pediococcus pentosaceus* so that lactic acid is produced in the fermented meat product. *Pediococcus pentosaceus* NRRL-B-11,465 is uniquely suited to making fermented meats.

The present invention relates to a meat fermentation method including the steps of providing lactic acid producing bacteria in the meat with an assimilable carbohydrate and with meat spoilage and rancidity inhibiting preservatives and then fermenting the meat with the bacteria so that lactic acid is produced from the carbohydrate over a period of time in the fermented meat the improvement which comprises: providing in admixture in meat a culture of a selected *Pediococcus pentosaceus* at a concentration of between about $10^5$ and $10^9$ of the *Pediococcus pentosaceus* per gram of meat with an assimilable carbohydrate, with meat spoilage and rancidity inhibiting amounts of preservatives including a hydroxyaryl antioxidant which preservatives substantially inhibit the *Pediococcus pentosaceus* at meat temperatures between 15.6° C. (60° F.) and 26.7° C. (80° F.) and with a stimulatory, food grade metal salt, preferably a manganese salt, in an amount sufficient to reduce the inhibition of the *Pediococcus pentosaceus* by the preservatives, wherein the selected *Pediococcus pentosaceus* culture is characterized by an ability to rapidly ferment in the meat admixture at meat temperatures between about 15.6° C. (60° F.) and 26.7° C. (80° F.) to produce a pH less than about 5; and fermenting the meat admixture at smokehouse temperatures between about 15.6° C. (60° F.) and 48.9° C. (120° F.) with the *Pediococcus pentosaceus* so that lactic acid is produced in the fermented meat product.

The present invention also relates to a culture adapted for meat fermentations including an assimilable carbohydrate at smokehouse temperatures between about 15.6° C. (60° F.) and 48.9° C. (120° F.) which comprises a selected *Pediococcus pentosaceus* grown in a growth medium including assimilable sources of carbon, nitrogen and inorganic substances, including preferably a manganese salt, to a concentration of at least about $1 \times 10^7$ of the *Pediococcus pentosaceus* per ml, having a pH between about 4 and 7 and containing a stimulatory, food grade metal salt after growth in an amount sufficient to accelerate the fermentation in the meat by providing a concentration of metal ion between about 0.01 ppm and 1500 ppm in the meat, wherein the selected *Pediococcus pentosaceus* culture is characterized by an ability to rapidly ferment in a meat admixture with an assimilable sugar and the preservatives at temperatures in a range between 15.6° C. (60° F.) and 26.7° C. (80° F.) to produce a pH less than about 5.

The metal salt is used in amounts of metal cation in the salt above about 0.01 ppm to about 1500 ppm by weight of the meat, preferably between about 0.1 and 100 ppm. The salt must be stimulatory and food grade. Such salts include for instance manganese chloride, manganese sulfate, manganese citrate, manganese glycerophosphate, manganese oxide and manganese gluconate and the various non-toxic metal salts of acids which are at least slightly soluble in water. Other metal ions include ferrous, ferric, magnesium, calcium, zinc; however, none are as effective as manganese. The metal salt can be incorporated into the culture in an amount between about 0.01 percent and 50 percent by weight of the culture in order to provide the amount of the metal salt needed in the meat when the culture is added.

The hydroxyaryl type antioxidant preservatives are usually added in amounts up to about 0.02 percent by weight of the meat, usually depending upon the amount of fat, to prevent rancidity. The most common hydroxyaryl antioxidants in the United States are BHT and BHA. Others which are used are nordihydroguaiaretic acid (NDGA), tertiary butyl hydroquinone (TBHQ), resin guaiac, propyl, octyl and dodecyl gallates, tocopherol and the like as described in Kirk-Othmer, Vol 2, pages 593-596 (1963).

The preferred *Pediococcus pentosaceus* strain of the persent invention has been deposited at the Northern Regional Research Laboratory of the USDA, Peoria, Ill. and has been designated as NRRL-B-11,465. NRRL-B-11,465 or a strain of the same species which has substantially the same low meat temperature fermentation characteristics is used in the present invention, such as those produced by genetic manipulation including mutation. For comparative purposes *Pediococcus pentosaceus* American Type Culture Collection No. 25744 is also described herein which ferments in meat in a manner similar to *Pediococcus cerevisiae*.

*Pediococcus pentosaceus* NRRL-B-11,465 was derived from a culture originally deposited at the American Type Culture Collection as ATCC 10791. This original culture was described as being most active at 26° C. in a standard culture broth; however, when selected members of this strain were used in a sausage fermentation, the fastest fermentation temperature was found to be 45° C. (113° F.). The inventor is uncertain as to whether NRRL-B-11,465: (1) is a mutant; or (2) is a selected single strain variant having anomalous low temperature fermentation characteristics.

The selected *Pediococcus pentosaceus* cells can be used as a concentrate containing at least about $1 \times 10^7$ cells per ml, usually between about $1 \times 10^9$ and $5 \times 10^{11}$ cells per ml mixed with the metal salt, preferably manganese salts. Concentrates with less than about $1 \times 10^7$ cells per ml require too much volume of culture because of excess water addition to the resultant sausage. The concentrate containing the metal salt can be frozen with or without a freezing stabilizing agent such as monosodium glutamate, malt extract, low fat dry milk, alkali metal glycerophosphates, glutamic acid, cystine, glycerol or dextran or the like and then thawed for use or it can be lyophilized to a powder as is well known to those skilled in the art. The cells are used at a rate between about $10^5$ to $10^9$ cells per gram of meat.

The low temperature *Pediococcus pentosaceus*, particularly NRRL-B-11,465, admixed with a stimulatory metal salt is also particularly adapted for nitrite reduction in fermented meats, particularly pork such as bacon and ham at a pH between about 5 and 6 and a concentration of bacteria between about $10^5$ and $10^{10}$ cells/ml. Usually the bacteria are included in the aqueous pickling solution and added to the meat as a spray or injected in an amount up to 15 percent by weight. Bacon is usually not reduced to a pH less than about 6 from an initial pH of 6.3 to 6.4. The *Pediococcus pentosaceus* can perform the nitrite reduction at lower temperatures than can be achieved with any known prior art Pediococcus.

SPECIFIC DESCRIPTION

EXAMPLE 1

*Pediococcus pentosaceus* NRRL-B-11,465 was grown in a growth medium such as described in U.S. Pat. Nos. 3,561,977 and 3,960,664. The medium includes a carbohydrate (glucose or other assimilable sugar), a nitrogen source (yeast extract or other source of amino acids) and traces of essential minerals or inorganic substances. The medium particularly included a manganese salt which was manganese sulfate monohydrate (formula weight 169.02) in the amount of 0.01 percent by weight. The pH of the medium was initially adjusted to between 6.5 to 6.7 and the fermentor was set to maintain a pH of 6.0 during the growth by the addition of ammonia. NRRL-B-11,465 was grown at 26° C. and at 32° C. for 11 hours to determine the effect of temperature on the growth conditions. For comparative purposes *Pediococcus pentosaceus* ATCC 25744 (which optimally grows at about 36° C.) was grown at 35° C. in the same medium.

The resulting cell concentrates were checked for cell count by growth on APT agar. For *Pediococcus pentosaceus* NRRL-B-11,465 at 26° C., about $1.7 \times 10^9$ cells per ml were produced and at 32° C., $1.3 \times 10^9$ cells per ml were produced. Thus the lower temperature appeared to be optimum in this growth medium for NRRL-B-11,465; however, growth temperature produced no essential difference in acid producing ability in sausage meat mix incubated at 25° C. (77° F.). For *Pediococcus pentosaceus* ATCC 25744 about $17 \times 10^9$ cells per ml were produced at 35° C. and it exhibited good growth at this temperature which was better than NRRL-B-11,465 at the lower temperatures. ATCC 25744 does not grow well at low temperatures (23° C.).

EXAMPLE 2

*Pediococcus pentosaceus* NRRL-B-11,465 and ATCC 25744 cells were used as the broth cultures of Example 1 without further concentration for making semi-dry sausage, without added manganese salt or any antioxidants, but with sodium chloride and sodium nitrite as preservatives. A commercially available culture of *Pediococcus cerevisiae* NRRL-B-5627 (now known as *Pediococcus acidilactici*) grown in the same medium as Example 1 without further concentration was also tested for comparative purposes. The purpose was to show that NRRL-B-11,465 was a unique culture, which produced a pH of 5.0 or lower in less than 30 hours at low meat temperatures. The ingredients for semi-dry sausage (typical summer sausage) and procedure were as follows:

Ingredients

| (1) Ground Meat Formulation | | |
|---|---|---|
| Beef | 6 lb | (2727 g) |
| Pork | 2 lb | (909 g) |
| Back Fat | 2 lb | (909 g) |
| | | 4545 g |
| (2) Cure | | |
| Dextrose | 1% | 45.5 g |
| NaCl | 3% | 136.5 g |
| NaNO$_2$ | 0.0156% | 0.709 g |
| (3.5 ml of a 200 mg/ml sol.) | | |
| (3) Spices | | |
| Ground black pepper | | 16.8 g |
| Whole Mustard Seeds | | 2.8 g |
| *-continued* | | |
| Nutmeg | | 1.4 g |
| Coriander | | 5.6 g |
| Allspice | | 1.4 g |
| (4) Maple liquid smoke (0.25% by weight in water) | | |
| | | 11.4 g |
| (5) Water | | |
| (at 4° C. and 2.5% by weight) | | 114 g |
| (6) Cultures as in Example 1 including: | | |
| (a) *Pediococcus pentosaceus* NRRL-B-11,465 grown at 26° C. and at 32° C. | | |
| (b) *Pediococcus pentosaceus* ATCC 25744 grown at 35° C. | | |
| (c) *Pediococcus cerevisiae* NRRL-B-5627 | | |

Procedure

The ingredients were mixed and divided into four batches of 1136 g (2.5 lb) each.

(1) An inoculation rate of $4.5 \times 10^7$ cells/g of meat (27.2 ml culture in 1136 g meat of 26° C. NRRL-B-11,465; 36 ml culture in 1136 g meat of 32° C. NRRL-B-11,465; 4.0 ml of culture in 1136 g meat of ATCC 25744 and 5.8 ml in 1136 g meat of NRRL-B-5627) was used. This introduced between 0.4 to 3 ppm of manganese sulfate monohydrate into the meat.

(2) The sausage mix was stuffed into casings which had a diameter of 55 mm.

(3) The stuffed sausage was dipped in a 2.5% solution of potassium sorbate.

(4) The fermentations were at 25° C. (77° F.) dry bulb, 23° C. (73.4° F.) wet bulb, (85% relative humidity).

(5) The heat treatment after 16 hours at 25° C. was 35° C. for 30 min; 48° C. for 30 min; 57° C. for 30 min; and finally heating to an internal meat temperature of 58° C. to 60° C. to eliminate trichinae.

The results for the semi-dry sausage produced are shown in Table 1.

TABLE 1

| Culture | Initial pH | pH after 16 hr. |
|---|---|---|
| *Pediococcus pentosaceus* | | |
| NRRL-B-11,465   26° C. | 5.83 | 4.72 |
| 32° C. | 5.84 | 4.79 |
| *Pediococcus pentosaceous* | | |
| ATCC 25744 | 5.83 | 5.64 |
| *Pediococcus cerevisiae* | | |
| NRRL-B-5627 | 5.82 | 5.46 |

Table 1 shows that *Pediococcus pentosaceus* NRRL-B-11,465 is much better than both *Pediococcus pentosaceus* ATCC 25744 and *Pediococcus cerevisiae* NRRL-B-5627 in lowering the pH at low meat temperatures. A pH of 5.0 was attainable after 12 to 14 hours at the 25° C. (77° F.) dry bulb and a 23° C. (73.4° F.) wet bulb temperature which was very unexpected. By comparison *Pediococcus cerevisiae* NRRL-B-5627, which is widely used commercially, was similar to ATCC 25744 at low meat temperatures in this time period and produced a pH of only about 5.46 in 16 hours at 26.7° C. (80° F.). Eventually, the pH will slowly begin to drop with these bacteria.

COMPARATIVE EXAMPLE 3

In a commercial Genoa sausage formulation including antioxidant preservatives and a concentrate of *Pediococcus pentosaceus* NRRL-B-11,465 essentially without any manganese, (all pork including by weight about 30% fat; 3.3% salt; 0.7% dextrose; 156 ppm nitrite;

Genoa spices; BHT and BHA 0.003% each, and citric acid 0.003% in a 74 mm casing), unexpectedly, it was found that a pH drop to 5.0 required 42 hours at 26.7° C. (80° F.) at 80% relative humidity which was extremely slow. Genoa sausage is regarded as a severe test of the fermentation characteristics of the culture.

It was determined that the formulation with the antioxidants in combination with the other preservatives severely inhibited NRRL-B-11,465 as can be seen from Example 4.

COMPARATIVE EXAMPLE 4

In tests in broth plus sodium chloride and/or BHT and BHA as antioxidants, it was found that these preservatives severely inhibited NRRL-B-11,465 at 37° C. (98.6° F.) over 2 hours as shown in the following Table 2. The higher temperatures were used to decrease the testing time.

TABLE 2

| Ingredient In Broth Medium | Reduction in Acid Production as Compared to Control | |
|---|---|---|
| | NRRL-B-11,465 | Pediococcus cerevisiae NRRL-B-5627 |
| BHT | 57.6% | Not Tested (NT) |
| BHA | 10.7% | (NT) |
| citric acid | 2.7% | (NT) |
| 3.0% NaCl | 36.2% | (NT) |
| 3.3% NaCl | 44.6% | (NT) |
| 3.6% NaCl | 49.5% | (NT) |
| BHT + BHT + citric acid (0.003% each) | 63.4% | 22.7% |
| BHT + BHT + citric acid (0.003% each + 3.3% NaCl | 83.0% | (NT) |

As can be seen from Table 2, there was substantial inhibition (more than 50%) by BHT alone. The most severe inhibition was with the combination of citric acid, BHT and BHA as antioxidants and sodium chloride. On a comparative basis, Pedicoccus cerevisiae NRRL-B-5627 was inhibited to a much lesser extent. This data gives an indication of what happened in the Genoa sausage, although the meat (particularly fats) tend to mask the inhibitory effect of the antioxidants to a certain degree.

Unexpectedly it was found that a metal salt in the meat reduced or eliminated the effects of BHT and/or BHA with sodium chloride to produce a much faster fermentation. It is uncertain why this occurs. It may be that the metal salt, particularly a manganese salt, reduces the initial lag time created by the effect of the preservatives on the bacteria. The results are shown in Example 5.

EXAMPLE 5

Manganese sulfate monohydrate was added with NRRL-B-11,465 as a centrifuged concentrate (containing insignificant amounts of any stimulatory metal salts because of the centrifugation) containing $1.22 \times 10^{11}$ cells per ml grown as in Example 1 in the meat to overcome the inhibitory effect of the BHT-BHA-citric acid antioxidant system in an amount of 100 ppm (32.5 ppm manganese ion) in the pork Genoa sausage formulation, (sodium chloride, 3.3%; 156 ppm sodium nitrite; dextrose, 0.7%; BHA, BHT and citric acid, 0.003% each by weight, in a 50 mm diameter casing). The manganese sulfate was added to the concentrate after it was diluted with water to $4.5 \times 10^7$ cells per ml and the mixture was added to the meat. The experiment was repeated four times with following typical results shown in Table 3.

TABLE 3

| | pH after hrs incubation @ 26.7° C. (80° F.) | | | | |
|---|---|---|---|---|---|
| | 0 | 24 | 26 | 28 | 30 |
| NRRL-B-11,465 | 6.1 | 5.68 | 5.71 | 5.40 | 5.33 |
| NRRL-B-11,465 plus 100 ppm MnSO$_4$ . H$_2$O | 6.1 | 5.28 | 5.04 | 4.92 | 4.88 |

As can be seen from Table 3, the manganese ion rapidly overcame the effect of the antioxidants.

EXAMPLE 6

The object of this experiment was to determine the pH profile of Genoa sausage inoculated with Pediococcus pentosaceus NRRL-B-11,465 including the manganese ion in the concentrate prior to dilution and incubated at 27° C. (80.6° F.) dry bulb and 24° C. (75.2° F.) wet bulb.

Ingredients
(1) Meat block
  20 lbs pork (Boston Butt)
(2) Cure and Spices

| Ingredient | (%) | (g/20 lbs (9.12 kg) |
|---|---|---|
| Salt (sodium chloride) | 3.3 | 300.0 |
| Spice mix | 1.08 | 98.3 |
| BHA, BHT and citric acid @ 0.003% by weight each | | |
| Sodium nitrite | 0.0156 | 1.42 |

(3) Cultures and inoculation rates
  (a) Pediococcus pentosaceus NRRL-B-11,465 with 6.97% by weight manganese ion in the culture which provides 13 ppm manganese ion in the meat. The concentrate (39 g) was diluted with 680 ml of tap water and 12.0 ml of the diluted culture per 5.0 lbs (2.3 kg) and 18.0 ml per 7.5 lbs (3.4 kg) was inoculated into the sausage mix ($2.6 \times 10^7$ cells per gm of meat). The concentrate had been centrifuged to $1.22 \times 10^{11}$ cells per ml and contained insignificant amounts of stimulatory metal salts prior to addition of the manganese salt.
  (b) Pediococcus cerevisiae NRRL-B-5627. The culture (28.5 g) was diluted with 680 ml of tap water and 11.8 ml of the diluted culture per 5.0 lbs (2.3 kg) was inoculated into the sausage mix ($2.6 \times 10^7$ cells per gram of meat). There were essentially no stimulatory amounts of metal salts in this concentrate.
  (c) Treatments

| Treatment | Weight |
|---|---|
| 1. Uninoculated control | 1136 g (2.5 lb) |
| 2. NRRL-B-5627 | 2273 g (5.0 lb) |
| 3. NRRL-B-11,465 | 3409 g (7.5 lb) |

Procedure
  (1) The meat was comminuted to the selected size.
  (2) The salt, spice mix, sodium nitrite, BHT and BHA were added to the comminuted meat and mixed.

(3) The sausage mix was divided into three (3) aliquots as follows:
  (a) 1.14 kg (2.5 lbs) (Uninoculated control).
  (b) 2.27 kg (5.0 lbs) (*Pediococcus pentosaceus*).
  (c) 3.41 kg (7.5 lbs) (*Pediococcus cerevisiae*).

(4) The sausage mix was stuffed into 74 mm diameter white fibrous casings using a hydraulic stuffer to a length of 4 inches (101.6 cm).

(5) The sausages were fermented at 27° C. (80.6° F.) dry bulb and 24° C. (75.2° F.) wet bulb (80% room humidity) using a controlled environmental chamber.

Determination of pH (1) The pH of the sausage was determined at 0, 16, 18, 20 and 22 hrs.

(2) Thirty grams of sausage were blended with 90 ml distilled water for 30 to 60 seconds. The pH of the slurry was determined. Prior to each pH reading, the pH meter was calibrated against two standard buffers (pH values of 7.00 and 4.01). The results are shown in Table 4.

TABLE 4

Comparison of pH values of Genoa sausage inoculated with *Pediococcus pentosaceus* NRRL-B-11,465 or *Pediococcus cerevisiae* NRRL-B-5627 and incubated at two temperatures (sausage initially at pH 6.0 (74 mm diameter).

| Treatment | Incubation Temperature | Incubation Time (Hours) | pH |
| --- | --- | --- | --- |
| *Pediococcus pentosaceus* NRRL-B-11,465 | 80° F. (26.7° C.) Dry bulb 75° F. (23.9° C.) Wet bulb | 20 | 5.00 |
| NRRL-B-5627 | 80° F. (26.7° C.) Dry bulb 75° F. (23.9° C.) Wet bulb | 38 | 5.65 |
| NRRL-B-11,465 | 85° F. (29.4° C.) Dry bulb 80° F. (26.7° C.) Wet bulb | 13 | 5.00 |
| NRRL-B-5627 | 85° F. (29.4° C.) Dry bulb 80° F. (26.7° C.) Wet bulb | 28 | 5.40 |

As can be seen from Table 4, NRRL-B-11,465 is much faster than NRRL-B-5627 even at the elevated temperatures. NRRL-B-11,465 with added manganese is also much faster than when manganese and NRRL-B-11,465 are added to the meat separately as per Example 5.

EXAMPLE 7

The object of this experiment was to determine if *Pediococcus pentosaceus* NRRL-B-11,465 controls growth of *Staphylococcus aureus* 265-1 in Genoa sausage incubated at 26.7° C. (80° F.) dry bulb and 23.9° C. (75° F.) wet bulb.

Procedure (1) The meat was maintained at 10° C. (50° F.).

(2) 2273 g (5 lbs) pork (Boston Butt) were comminuted in a blender.

(3) Toward the end of the chopping period, 75 g (3.3%) salt; 24.6 g (1.08%) spices; 0.003% each of BHT, BHA and citric acid; and 1.70 ml (156 ppm) of a 200 mg/ml solution of sodium nitrite were added to the meat to provide the Genoa sausage mix.

(4) Two 1000 g aliquots were prepared from the Genoa sausage mix.

(5) *Staphylococcus aureus* strain 265-1, was inoculated into each aliquot of the sausage mix as an 18 hr broth culture (Difco BHI$_{t.m.}$ medium) incubated at 35° C. (The culture had been transferred successively three times).

(6) Thirty-nine grams of NRRL-B-11,465 culture was diluted with 680 ml tap water and was added to one sausage mix aliquot at a rate of 5.3 ml diluted culture per 1000 g sausage mix.

(7) Sufficient *Staphylococcus aureus* strain 265-1 was added to both sausage mix aliquots to provide approximately 10,000 viable cells of sausage mix. Each sausage mix aliquot was thoroughly mixed with gloved hands (sterile surgical gloves).

(8) Each aliquot was stuffed into fibrous casings 74 mm diameter. Links (12–18 cm long) were formed for the various sampling times.

(9) The sausage links were dipped in a 2.5% solution of potassium sorbate.

(10) The sausage links were fermented at 27° C. 80.6° F.) dry bulb and 24° C. (75.2° F.) wet bulb in a controlled environmental chamber.

Determination of pH

Thirty grams of sausage were blended with 90 ml distilled water for 30 to 90 seconds. The pH of the slurry was measured using a pH meter. Prior to each pH measurement the pH meter was calibrated against 2 standard buffers (pH values of 7.00 and 4.01).

Enumeration of *Staphylococcus aureus*

(1) Samplings for the enumeration of *Staphylococcus aureus* were made on the 0 hr sausage mix and on the sausage after it had fermented for 21 hr.

(2) Ten gram samples were taken from a ring (0.5 to 1.0 cm thick) around the outer portion of the sausage.

(3) Each 10 g sample was blended for 2 min. with 0.1% Peptone (Difco$_{t.m.}$) water. Further decimal dilutions (1/10 each) were performed with the same diluent. Aliquots of 0.1 ml of the dilutions were surface spread onto freshly (24 hr) prepoured, dried surface Baird-Parker (BP)$_{t.m.}$ Agar plates in duplicates. The agar plates were incubated at 35° C. (95° F.) for 48 hr. Plates containing 20 to 200 colonies were selected and only typical *Staphylococcus aureus* (black surrounded by an opaque zone with an outer clear zone) were counted.

Results (1) Table 5 shows the viable counts of *Staphylococcus aureus* strain 265-1 in the periphery of Genoa sausage resulting from the different treatments.

(2) Table 6 shows pH of Genoa sausage in the various treatments.

TABLE 5

Effect of NRRL-B-11,465 on growth of *Staphylococcus aureus* 265-1 in the periphery of Genoa sausage incubated at 27° C. (80.6° F.) for 21 hours.

| | CFU of *S. aureus*/g of meat at time | |
| --- | --- | --- |
| | 0 hr | 21 hr |
| *Staphylococcus aureus* 265-1 only | 14,000 | 1,600,000 |
| *Staphylococcus aureus* 265-1 & NRRL-B-11,465 | 11,000 | 150,000 |

TABLE 6 pH in Genoa inoculated with *Staphylococcus aureus* 265-1 only and NRRL-B-11,465 incubated at 27° C. (80.6° F.) for 21 hours.

|  | pH | |
| --- | --- | --- |
|  | 0 hr | 21 hr |
| *Staphylococcus aureus* 265-1 | 6.0 | 5.95 |
| *Staphylococcus aureus* 265-1 & NRRL-B-11,465 | 6.0 | 4.80 |

In Genoa sausage inoculated with 10,000 *Staphylococcus aureus* 265-1 per gram and fermented for 21 hours at 27° C. (80.6° F.) dry bulb and 24° C. (75.2° F.) wet bulb, *Pedicoccus pentosaceus* NRRL-B-11,465 controlled the growth of *Staphylococcus aureus* in periphery to only a one log increase after 21 hours which is a very good result. It will be recognized that levels of contamination with *Staphylococcus aureus* above $10^5$ cells per gram of meat are unacceptable in a food product.

Other metal ions were evaluated in Genoa sausage as shown in Table 7, including calcium, magnesium, ferrous and ferric, zinc ions, using the procedure, meat formulations and centrifuged culture of *Pediococcus pentosaceus* NRRL-B-11,465 of Example 6, particularly with BHT and BHA as antioxidants in the meat.

TABLE 7

| Metal Ion | Time(hours) | | | |
| --- | --- | --- | --- | --- |
|  | 19 | 20 | 21 | 26 |
| $Ca^{+2}$ | 5.55 | — | 5.42 | 5.2 |
| $Fe^{+2}$ | 5.65 | — | 5.55 | 5.4 |
| $Fe^{+3}$ | 5.7 | — | 6.3 | 5.5 |
| $Zn^{+2}$ | 5.72 | — | 5.7 | 5.5 |
| $Mg^{+2}$ | 5.7 | — | 5.7 | 5.55 |
| $Mn^{+2}$ | 5.19 | 5.09 | 4.96 | — |
| $Mg^{+2} + Mn^{+2}$ (6.5 ppm each) | 5.17 | 5.07 | 4.93 | — |
| Control (no culture) | — | — | 5.9 | — |
| Control (with culture and no metal ion added) | — | — | 5.7 | — |

Calcium was the most stimulatory. After 21 hours the pH of the sausage was 5.22 with added calcium ion compared to a pH of 5.09 after 20 hours with an equivalent amount of added manganese. The other salts were minimally stimulatory at this metal ion concentration and can be used at higher metal ion levels to achieve more rapid fermentation. Without a stimulatory amount of a metal salt, the culture was not effective at 27° C. (80.6° F.) as can be seen from Table 7. It would be effective at longer times or at higher meat temperatures.

Conclusion

Thus it can be seen that the selected cultures of low temperature *Pediococcus pentosaceus*, particularly NRRL-B-11,465 are unique in their ability to ferment with a stimulatory food grade metal salt in meat particularly in the presence of preservatives, including hydroxyaryl type antioxidants and salt. *Pediococcus pentosaceus* NRRL-B-11,465 is unique because of the rapidity of the fermentation at elevated temperatures which are used for such fermentations by the prior art, regardless of whether or not the metal salt is used.

I claim:

1. The improvement in a meat fermentation method including the steps of providing lactic acid producing bacteria in the meat with an assimilable carbohydrate and then fermenting the meat with the bacteria so that lactic acid is produced from the carbohydrate over a period of time in the fermented meat which comprises:

(a) providing in admixture in meat a culture of a selected *Pediococcus pentosaceus* with an assimilable carbohydrate and with a stimulatory, food grade metal salt in an amount sufficient to accelerate the fermentation by the *Pediococcus pentosaceus*, wherein the selected *Pediococcus pentosaceus* culture has the meat fermentation characteristics of *Pediococcus pentosaceus* NRRL-B-11,465 and is characterized by an ability to rapidly ferment in the meat admixture at meat temperatures between about 15.6° C. and 26.7° C. to produce a pH less than about 5; and (b) fermenting the meat admixture at temperatures between about 15.6° C. and 48.9° C. with the *Pediococcus pentosaceus* so that lactic acid is produced in the fermented meat product.

2. In a meat fermentation method including the steps of providing lactic acid producing bacteria in the meat with an assimilable sugar and with meat spoilage and rancidity inhibiting preservatives and then fermenting the meat with the bacteria so that lactic acid is produced from the sugar over a period of time in the fermented meat the improvement which comprises:

(a) providing in admixture in meat a culture of a selected *Pediococcus pentosaceus* at a concentration of between about $10^5$ and $10^9$ of the *Pediococcus pentosaceus* per gram of meat with an assimilable carbohydrate, with meat spoilage and rancidity inhibiting amounts of preservatives including a hydroxyaryl antioxidant which preservatives substantially inhibit the *Pediococcus pentosaceus* at meat temperatures between 21.1° C. and 26.7° C. and with a stimulatory, food grade metal salt in an amount sufficient to reduce the inhibition of the *Pediococcus pentosaceus* by the preservatives, wherein the selected *Pediococcus pentosaceus* culture has the meat fermentation characteristics of *Pediococcus pentosaceus* NRRL-B-11,465 and is characterized by an ability to rapidly ferment in the meat admixture at meat temperatures between about 15.6° C. and 26.7° C. to produce a pH less than about 5; and (b) fermenting the meat admixture at smokehouse temperatures between about 15.6° C. and 48.9° C. with the *Pediococcus pentosaceus* so that lactic acid is produced in the fermented meat product.

3. The method of claim 2 wherein the meat admixture contains the hydroxyaryl antioxidants butylated hydroxytoluene, butylated hydroxyanisole, tertiary butyl hydroquinone or mixtures thereof as preservatives.

4. The method of claim 1 wherein the meat admixture contains a food grade nitrite as a preservative which is partially reduced due to the lactic acid produced by the *Pediococcus pentosaceus*.

5. The method of claim 2 wherein the *Pediococcus pentosaceus*, sugar, preservatives and metal salt are added to the meat as an aqueous pickling solution containing between about $10^5$ to $10^{10}$ *Pediococcus pentosaceus* per ml in an amount of the pickling solution up to about 15 percent by weight based upon the meat weight and wherein the meat is held at 21.1° C. to 38° C. until a pH between about 5 and 6 is achieved.

6. The method of claim 1 or 2 wherein metal salt is a manganese salt and wherein the fermented meat product is sausage, which is fermented at meat temperatures of 26.7° C. or less to produce a pH of less than about 5.

7. The method of claim 1 or 2 wherein the *Pediococcus pentosaceus* has essentially the identification characteristics of NRRL-B-11,465.

8. The method of claim 1 or 2 wherein the *Pediococcus pentosaceus* is NRRL-B-11,465.

9. The method of claim 1 or 2 wherein the *Pediococcus pentosaceus* culture has been grown in the presence of a manganese salt and further manganese salt is added to the culture as the metal salt after growth which is then admixed with the meat as a liquid concentrate containing at least about $10^7$ cells per ml.

10. The method of claim 9 wherein the bacterial concentrate is frozen with the manganese salt prior to use and thawed to provide a liquid concentrate for admixture with water prior to addition to the meat.

11. The method of claim 1 or 2 wherein the *Pediococcus pentosaceus* cells are in a lyophilized, powdered form containing a manganese salt as the metal salt which is provided in the meat as a powder.

12. A culture of *Pediococcus pentosaceus* adapted for meat fermentations including an assimilable carbohydrate at smokehouse temperatures between about 15.6° C. and 48.9° C. which comprises a selected *Pediococcus pentosaceus* grown in growth medium including assimilable sources of carbon, nitrogen and inorganic substances to a concentration of at least about $1 \times 10^7$ of the *Pediococcus pentosaceus* per ml, having a pH between about 4 and 7 and said culture containing a stimulatory food grade metal salt after growth in an amount sufficient to accelerate the fermentation in the meat by providing a concentration of metal ion between about 0.01 ppm and 1500 ppm in the meat, wherein the selected *Pediococcus pentosaceus* culture has the meat fermentation characteristics of *Pediococcus pentosaceus* NRRL-B-11,465 and is characterized by an ability to rapidly ferment in a meat admixture with an assimilable sugar at temperatures in a range between 15.6° C. and 26.7° C. to produce a pH less than about 5.

13. The culture of claim 12 wherein the *Pediococcus pentosaceus* has essentially the identification characteristics of NRRL-B-11,465 and has been grown in the presence of a manganese salt as the metal salt.

14. The culture of claim 12 wherein the *Pediococcus pentosaceus* is NRRL-B-11,465.

15. The culture of claim 12 containing between about $10^9$ and $10^9$ *Pediococcus pentosaceus* per ml and a manganese salt as the metal salt.

16. The culture of claim 12 wherein the growth medium contains a manganese salt, in an amount sufficient to facilitate the growth of the cells in the medium.

17. The culture of claim 12 wherein the metal salt is a manganese salt.

18. In a meat fermentation method including the steps of providing lactic acid producing bacteria in the meat with an assimilable carbohydrate and then fermenting the meat at temperatures between 15.6° C. and 48.9° C. with the bacteria so that lactic acid is produced from the carbohydrate over a period of time in the fermented meat, the improvement which comprises:

providing a *Pediococcus pentosaceus* which has the meat fermentation characteristics of *Pediococcus pentosaceus* NRRL-B-11,465 and the ability to ferment in the meat with a stimulatory food grade metal salt in amount sufficient to accelerate the fermentation at meat temperatures between 15.6° C. and 26.7° C. to produce a pH less than about 5 in the meat.

19. The method of claim 18 wherein the *Pediococcus pentosaceus* is NRRL-B-11,465.

* * * * *

UNITED STATES PATENT AND TRADEMARK OFFICE
CERTIFICATE OF CORRECTION

PATENT NO. : 4,303,679
DATED : December 1, 1981
INVENTOR(S) : Moshe Raccach

It is certified that error appears in the above-identified patent and that said Letters Patent are hereby corrected as shown below:

Column 7, line 30, "BHT" second occurrence, should be --BHA--.

Column 7, line 32, "BHT" second occurrence, should be --BHA--.

Column 14, Claim 15, line 11 "$10^9$" second occurrence should be --$10^{11}$--.

Signed and Sealed this

Fifth Day of October 1982

[SEAL]

Attest:

GERALD J. MOSSINGHOFF

Attesting Officer     Commissioner of Patents and Trademarks